United States Patent [19]

Schneider et al.

[11] Patent Number: 4,794,197

[45] Date of Patent: Dec. 27, 1988

[54] ALL-CIS-1,3,5-TRIAMINO-2,4,6,-CYCLOHEXANETRIOL DERIVATIVES, THEIR USE, PROCESSES FOR THEIR PREPARATION AND PHARMACEUTICAL PREPARATIONS CONTAINING THEM

[76] Inventors: Walter Schneider; Isidor Erni; Hans K. Hegetschweiler, c/o Laboratorium für anorganische Chemie, Eidgenössische Technische Hochschule Zürich, ETH-Zentrum, Universitätsstrasse 6, CH-8092 Zürich, Switzerland

[21] Appl. No.: 824,950

[22] Filed: Jan. 31, 1986

[30] Foreign Application Priority Data

Feb. 2, 1985 [DE] Fed. Rep. of Germany ....... 3503614

[51] Int. Cl.$^4$ .................... C07C 87/36; C07C 103/19
[52] U.S. Cl. ................ 564/152; 260/502.5 R;
546/333; 546/334; 546/337; 548/342; 558/166;
558/170; 558/430; 560/29; 560/43; 560/125;
562/452; 562/507; 564/153; 564/170; 564/191;
564/217; 564/281; 564/282; 564/285; 564/287;
564/290; 564/374; 564/453; 564/457; 564/461
[58] Field of Search .............. 564/281, 282, 285, 287,
564/290, 374, 453, 457, 461, 152, 170, 191, 217,
153; 546/333, 334, 337; 548/342; 260/502.5 R;
558/166, 170, 430; 560/29, 43, 125; 562/452,
507

[56] References Cited

U.S. PATENT DOCUMENTS 3,496,196  2/1970  Suami et al. .................... 564/461

FOREIGN PATENT DOCUMENTS 2360176  6/1975  Fed. Rep. of Germany .

Primary Examiner—Glennon H. Hollrah
Assistant Examiner—John A. Sopp
Attorney, Agent, or Firm—Foley & Lardner, Schwartz, Jeffery, Schwaab, Mack, Blumenthal & Evans

[57] ABSTRACT

All-cis-1,3,5-Triamino-2,4,6-trihydroxycyclohexane derivatives corresponding to the general formula I

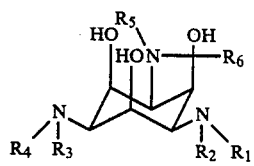

wherein the symbols $R_1$, $R_2$, $R_3$, $R_4$, $R_5$ and $R_6$ are identical or different and represent hydrogen atoms, alkyl groups or —CO-alkyl groups wherein the alkyl in the alkyl or —CO-alkyl group has 1 to 18 carbon atoms and the alkyl and —CO-alkyl groups may contain, independently of one another, one or more identical or different functional groups, and at least one of the groups $R_1$ to $R_6$ is one of the above mentioned unsubstituted or substituted alkyl groups or —CO-alkyl groups, and their salts with pharmacologically conventionally used inorganic or organic acids and their quaternary ammonium salts, processes for their preparation and their use, and pharmaceutical preparations containing these compounds.

18 Claims, No Drawings

ALL-CIS-1,3,5-TRIAMINO-2,4,6,-CYCLOHEXANETRIOL DERIVATIVES, THEIR USE, PROCESSES FOR THEIR PREPARATION AND PHARMACEUTICAL PREPARATIONS CONTAINING THEM

The present invention relates to new all-cis-1,3,5-triamino-2,4,6-cyclohexanetriol derivatives, also referred to as cis-1,3,5-triamino-1,3,5-trideoxy-inositol, to processes for their preparation, to pharmaceutical preparations containing these derivatives and/or the known parent substance, all-cis-1,3,5-triamino-2,4,6-cyclohexanetriol, and to the use of these derivatives and of the parent substance for the preparation of medicaments to be used therapeutically in cases of excessively high iron levels in the animal and particularly the human body. The invention also relates to the use of the above mentioned derivatives (ligands) for dissolving other unwanted iron deposits. Further, the invention relates to the use of the abovementioned ligands for other metal ions, on particular as ion carriers in ion-selective electrodes (see "Ion-selective electrodes", Cambridge University Press, Cambridge, (1983)) or for therapeutic or diagnostic applications (see Inorganic Chemistry in Biology and Medicine, ACS Symposium Series 140, American Chemical Society, Washington, D.C. (1980) pages 121 to 140, 91 to 101 and 103 to 119).

Iron is widely distributed in biological systems and takes part in important biochemical reactions. The body of a healthy adult contains about 4 g of iron. More than half this quantity (about 2.6 g) is present in the haemoglobin and the red blood corpuscles. Various disturbances of iron metabolism occur in humans. Iron deficiency is relatively common but rarely gives rise to serious ill health. Excess iron levels are found more rarely but their effects on health are much more serious. The body can only get rid of iron by sloughing off cells (dead cells from the skin and the intestinal wall) and by blood loss. Excessive amounts of iron absorbed into the system can initially be stored in special depots but if their capacity is exceeded the iron begins to have a toxic effect. The resulting pathological condition is known as haemochromatosis or haemosiderosis. It may be caused, for example, by a disturbance in the regulation of iron uptake in the form of excessive resorption in later years (after about 40). It may also occur, for example, in patients suffering from certain blood diseases which could hitherto only be treated by frequent blood transfusions which also lead to excess iron levels. An example of such a disease is $\beta$-thalassaemia (see Inorganic Chemistry in Biology and Medicine, ACS Symposium Series 140, American Chemical Society, Washington, D.C. (1980), pages 251 to 261). The continuous supply of iron is then deposited in various organs as insoluble iron(III) hydroxide (or iron hydroxide, iron oxide, rust). Such deposits of iron hydroxide may lead to early death even at the age of 20 to 25 years.

These depositions of iron hydroxide can be delayed by the administration of complex formers (ligands) which are capable of eliminating iron from the body in a soluble form. It is known to administer 30-amino-3,14,25-trihydroxy-3,9,14,20,25-pentaaza-2,10,13,21,24-triacontane-pentanone-methane sulphonate (Deferoxamine) for this purpose (see FR 694M and Inorganic Chemistry in Biology and Medicine, ACS Symposium Series 140, American Chemical Society, Washington, D.C. (1980), pages 279 to 312).

This has, however, the following disadvantages: Existing deposits may be dissolved at the same time; the drug must be administered parenterally; the half life in the body is very short and continuous injection is therefore necessary; the compounds are very difficult to obtain; there are indications of serious side effects after prolonged administration (visual disturbances).

It is therefore an object of the present invention to find ligands which should as far as possible fulfil the following conditions:

1. High selectivity for Fe(III) in order to minimise side effects and form sufficiently stable complexes in the physiological medium to prevent the precipitation of iron hydroxides.
2. Capacity for sufficiently rapidly dissolving the iron hydroxides.
3. Low toxicity of ligand and complex.
4. Sufficiently slow degradation of ligand and complex in the body to enable excretion to take place.
5. Oral administration possible.

The general criteria for fulfilling condition 1 have been discussed in some detail in the recent literature (see Inorganic Chemistry in Biology and Medicine, ACS Symposium Series 140, American Chemical Society, Washington, D.C. (1980), pages 279 to 312). It has now been found that the cyclohexane derivatives defined hereinafter fulfil both conditions 1 and 2 optimally and conditions 3 to 5 to a high degree. They are eminently suitable for bringing iron and other metals into solution by complex formation and in particular for eliminating them from the human and animal body.

The following factors are decisive for good complex formation:

(a) All-axial position of the oxygen atoms on the cyclohexane ring so that optimum $O_6$-coordination of the iron can be achieved by two ligands or one ligand substituted by functional groups. The all-axial position is brought about by three ammonium groups (alkylated or protonated).

(b) Acidification of the hydroxyl groups by about 8 pK-units compared with conventional aliphatic alcohols by positive charges of the nitrogen atoms on the cyclohexane ring which are protonated in the neutral region or quaternized.

If these two conditions are not fulfilled, trihydric and higher hydric alcohols do not give stable complexes with iron in the neutral range.

The present invention therefore relates to the new compounds defined in the claims.

As is well known to the chemist, these compounds only have those combinations of substituents which are possible on steric grounds.

The parent substance of these new compounds, all-cis-1,3,5-triamino-2,4,6-cyclohexanetriol, is already known. The synthesis of this compound by hydrogenation of 1,3,5-triaminophloroglucinol (2) has been repeatedly described (G. Quadbeck, E. Röhm, Chem. Ber. 89, 1645–1648 (1956); F. W. Lichtenthaler, H. Leinert, Chem. Ber. 99, 903–907 (1966); G. Bracher, Diploma work ETH Zürich (1973)). The authors first prepared the unstable and explositive trinitrosophloroglucinol, which they then oxidized to trinitrosophloroglucinol with fuming nitric acid. This reaction can only be carried out in quantities amounting to grams and is therefore unsuitable for large scale application. The direct nitration of phloroglucinol has only been published in very recent times (A. A. DeFusco, A. T. Nielson, R. L. Atkins, Org. Prep. Proceed. Int. 14, 393–424 (1982)).

This is a delicate, precarious reaction. No pharmaceutical use or application of this parent compound has yet been disclosed, however. Since the known methods of preparation are very unsatisfactory, as indicated above, it is an object of the present invention to find new and improved as well as simplified processes for the preparation of this compound and its derivatives. The present invention therefore also relates to the processes of preparation defined in the claims.

The new compounds according to the invention have a relatively low toxicity and can be administered intravenously and in some cases also orally.

The above-mentioned, known parent compound of the new compounds according to the invention, which has not hitherto been recommended as a pharmaceutical product, also has a relatively low toxicity and is also effective in bringing iron into solution by complex formation.

The present invention thus relates to pharmaceutical preparations containing all-cis-1,3,5-triamino-2,4,6-cyclohexanetriol or compounds corresponding to formulae I to VI according to claim 1 as active constituent, optionally together with conventional pharmaceutical diluents, additives or excipients.

The preparation should be administered 1 to 3 times per day (or per week).

The compounds may be made up into suitable pharmaceutical formulations in the usual manner as required.

1,3,5-Triamino-2,4,6-cyclohexanetriols may exist in ten different diastereomeric forms with respect to the position of the nitrogen and oxygen atoms. It is the so-called all-cis-1,3,5-triamino- or -trialkylamino-2,4,6-cyclohexanetriol of the formula according to the claims which is of interest according to the invention. This may be represented in a simplified form as follows:

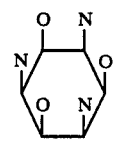

According to the invention, the desired all-cis-1,3,5-triamino-2,4,6-cyclohexanetriols may be prepared according to the following reaction scheme, whereby the disadvantages of the previous methods of synthesis can be obviated:

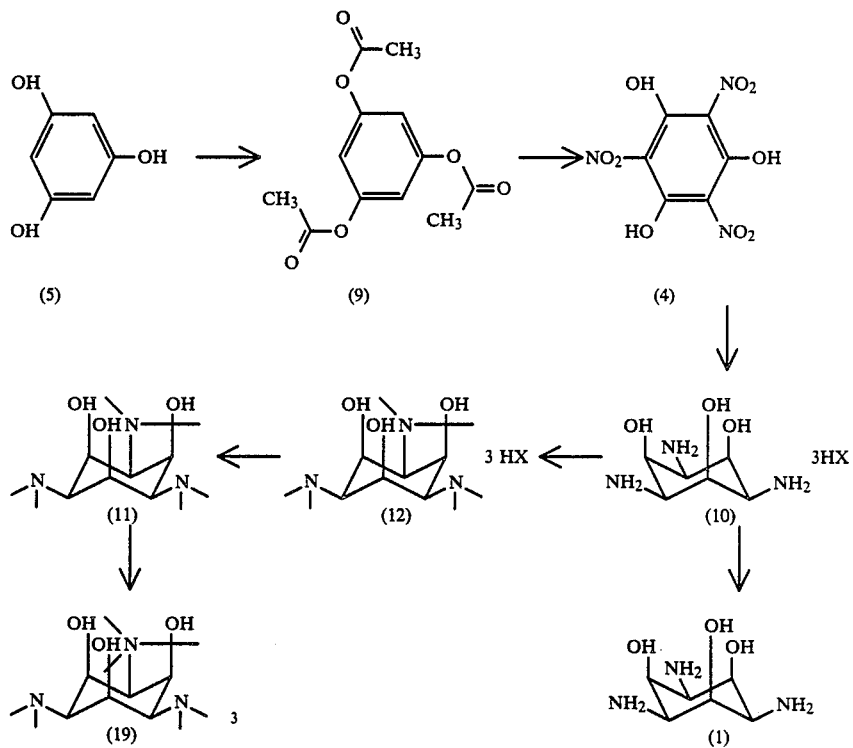

It has been shown experimentally that a grain of β-FeO(OH) measuring 50×6×6 nm can be dissolved five times more rapidly by the compound according to the invention corresponding to the general formula I wherein $R_1=R_2=R_3=R_4=R_5=R_6=CH_3$ than by the known compound, deferoxamine.

The compounds used according to the invention are suitably administered in doses each containing 1 to 50 mg of active constituent per kilogram of body weight. 1-10 mg/kg is sufficient for chronic detoxification and up to 50 mg/kg may be administered for acute detoxification.

This invention thus relates to a process of preparation in which phloroglucinol (5) is converted virtually quantitatively into the triacetate (9) by means of acetic anhydride of the method of Heller, Berichte 45, 421 (1912). When the compound is thus protected, the process of nitration according to Nietzki and Moll, Berichte 26, 2185–2187 (1893) in fuming nitric acid can be carried out safely. The moderately water-soluble tripotassium salt obtained may, for example, be precipitated as a difficultly soluble barium salt which can then easily be obtained in a pure form. The addition of a stoichiometric quantity of acid, e.g. sulphuric acid, then releases the desired trinitrophloroglucinol (4).

The trinitrophloroglucinol is subsequently hydrogenated. Thus whereas it was previously necessary to isolate the triaminophloroglucinol, which is extremely sensitive to oxygen, this can now be obviated without any loss of purity or yield. Instead of free phenol (4), a mono-alkali metal salt thereof may be used, in particular the potassium salt.

The process of hydrogenation is carried out with vigorous stirring sufficient to produce turbulence. A mixture of various polyhydroxy-polyamino-cyclohexanes is obtained, from which the desired all-cis-1,3,5-triamino-2,4,6-cyclohexanetriol can be isolated in the form of a salt, e.g. the sulphuric acid salt (10a) by repeated recrystallization, e.g. from water-methanol.

Various salts may be prepared from the sulphate (10a) originally obtained, e.g. the trichloride (10b) or the triformate (10c) or the free base (1), for example by ion exchange using an anion exchange resin. Alternatively, stoichiometric reaction of the sulphate (10a) with barium hydroxide also leads to (1).

The N-alkylated and N-acylated compounds may be obtained by alkylation or acylation of the free amine or of a salt thereof. The usual substances suitable for alkylating or acrylating amines may be used.

Examples of suitable alkylating agents include alkyl halides (e.g. bromides and iodides) having 1 to 18 carbon atoms (e.g. methyl, ethyl, n-propyl, isopropyl, n-butyl, sec.-butyl and tert.-butyl iodide or bromide). Examples of olefines and alcohols which may be used for alkylation by addition or condensation include olefines having 1 to 18 carbon atoms (e.g. those containing activating substituents such as nitrile groups, e.g. acrylonitrile) and alcohols with 1 to 18 carbon atoms (e.g. those containing activating substituents such as nitrile groups, e.g. glycollic acid nitrile). Reductive alkylation with aldehydes and ketones containing 1 to 18 carbon atoms may also be carried out.

Examples of acylating agents include reactive derivatives of alkanoic acids containing 1 to 18 carbon atoms in the alkyl moiety, such as acid halides, in particular acid chlorides, acid anhydrides and esters. Acetyl chloride, propionyl chloride, caprylic acid chloride and succinic acid anhydride are specific examples.

The alkylating and acylating agents may be substituted by one or more identical or different functional groups or their precursors, in particular those which can be coordinated on metal cations, in particular or iron(III). Such functional groups may be present in a masked form, particularly when there is a risk of their being affected by the alkylating or acylating conditions employed or of their taking part in the reaction.

The following are examples of such substituents: Hydroxyl groups, carbonyl groups (and their derivatives such as salts, amides and esters and the nitrile group as their precursor), —CON(OH)R wherein R denotes an alkyl group having 1 to 6, in particular 1 to 4 carbon atoms, —OPO₃H and salts and esters thereof, —PO₃H and its salts and esters, —SR, wherein R has the same meaning as in —CON(OH)R, —CN, and

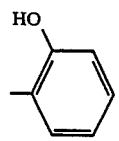

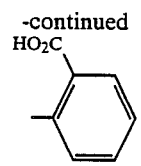

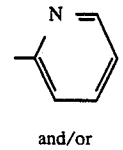

and/or

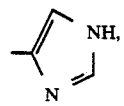

and/or salts thereof.

For the preparation of the diether derivatives corresponding to the general formula III, the all-cis-1,3,5-triamino-2,4,6-trihydroxy-cyclohexanone compounds may be reacted in the form of their quaternized derivatives (for example of formula II) with the corresponding difunctional alkylating agents, e.g. alkylene halides, e.g. methylene or ethylene halides (e.g. bromides or iodides). The reaction is preferably carried out in the presence of strong bases such as alcoholates, e.g. alkali metal and/or alkaline earth metal methoxide or ethoxide in the corresponding alcohol as solvent.

Preparation of the diamine derivatives corresponding to the general formula IV is carried out by alkylation of the all-cis-1,3,5-triamino-2,4,6-trihydroxycyclohexane derivatives corresponding to the general formula I with a difunctional alkylating agent, e.g. an alkyl halide having 4 to 8 methylene groups. Instead of using amines of formula I, complexes of 2 molecules thereof with iron(III) or chromium(III) may be used as starting material.

When alkylating agents with short chained alkyl groups are used, in particular the methyl group, alkylation of the free amines or of their salts generally results in secondary amines. This alkylation may be continued to the state of quaternization. When alkylating agents are used for introducing longer chained, secondary or tertiary alkyl groups and for introducing alkyl groups with bulky substituents, the corresponding primary amine derivatives are generally obtained.

Reductive alkylation with aldehydes and ketones is particularly suitable for the preparation of tris-(dialkylamino) compounds ((11). The tris-(dialkylamino) compounds (11) may be prepared, for example, by alkylating the salt 10 (e.g. the sulphate, trichloride or triformate). The following alkylating methods, for example, may be used:

(a) Reductive alkylation with aldehydes or ketones (e.g. formaldehyde, acetaldehyde, propionaldehyde, acetone) and formic acid by the method of Leuckart-Wallach. The desired amine (12) may be isolated as the hydrochloride in yields of up to 50% by repeated recrystallisation, e.g. from alcohol (e.g. methanol).

(b) Reductive alkylation with aqueous aldehyde or ketone solution (e.g. formaldehyde, acetaldehyde, propionaldehyde or acetone solution) and platinum/hydrogen as reducing agent. This reaction gives rise exclusively to the desired stereoisomer (11) in high yields. For example, all-cis-1,3,5-tris-(dimethylamino)-2,4,6-cyclohexanetriol was isolated in each case as the hydrochloride (12a) or sulphate (12b). The free triamine (11) could be obtained in the form of the monohydrate by ion exchange with hydroxide. In this form, the solubility in many organic solvents is only slight. Boiling under reflux in hexane yields the anhydrous product which is readily soluble in all conventional solvents, presumably due to special structural characteristics (hydrogen bridges).

The alkylation products obtained may be quaternized by alkylation. For example, the reaction with alkyl halides such as methyl, ethyl, propyl, isopropyl or butyl halides (e.g. iodides, bromides and chlorides) results in the corresponding mono-, di- and tri-quaternary products in accordance with the following reaction scheme:

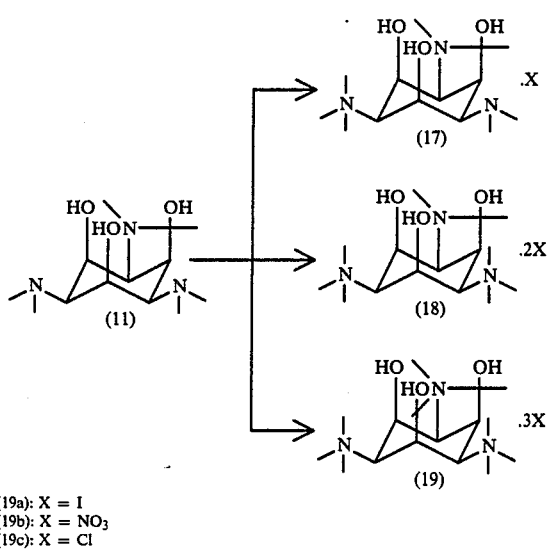

(19a): X = I
(19b): X = NO$_3$
(19c): X = Cl

For example, all-cis-1,3,5-tris-(dimethylamino)-2,4,6-cyclohexanetriol (11) could be converted to the di- and triquaternary products (18) and (19a) by reaction with methyl iodide as quaternizing agent. The monoquaternary compound (17) could also be isolated.

The triquaternary iodide (19a) can be separated from the precipitating mixtures by recrystallisation, e.g. from a weakly alkaline aqueous solution of (17) and (18).

Triquaternization may also be carried out, for example, in an alkaline aqueous solution of all-cis-1,3,5-tris-(dimethylamino)-2,4,6-cyclohexanetriol with an excess of bromohydrins or expoxides (e.g. bromoethanol or ethylene oxide). The pH for this reaction is preferably adjusted to about 10 by the addition of alkali.

The compounds according to the invention, particularly those in which R$_1$-R$_6$ or R$_7$-R$_9$ represent —CO-alkyl, may also be prepared by the method of F. W. Lichtenthaler, and H. Leinert, Chem. Ber. 99, 903–907 (1966) (where the compound corresponding to the general formula I wherein R$_1$=R$_3$=R$_5$=—COCH$_3$ and R$_2$=R$_4$=R$_6$=H is described).

Pharmaceutically suitable salts of the compounds according to the invention include salts formed with an organic acid (e.g. an acetate, maleate, tartrate, methane sulphonate, benzene sulphonate, formate or toluene sulphonate) or with an inorganic acid (e.g. chloride, bromide, sulphate or phosphate).

The pharmaceutical compositions according to the invention which contain one or more of the compounds according to the invention may be, for example, solid or liquid and may be presented in pharmaceutical forms of the kind commonly used in human and veterinary medicine, e.g. as simple or coated tablets, capsules, including gel capsules, granulates, suppositories and preparations suitable for injection. They are prepared by the usual methods. The active ingredient or ingredients may be introduced with the aid of excipients normally used in such pharmaceutical compositions, such as talcum, gum arabic, lactose, starch, magnesium stearate, cocoa butter, aqueous or non-aqueous carriers, fatty substance of animal or vegetable origin, paraffin derivatives, glycols, various wetting, dispersing or emulsifying agents, and preservatives.

Examples of metal ions for which the compounds according to claim 1 and/or all-cis-1,3,5-triamino-2,4,6-cyclohexanetriol may be used as mentioned above include alkaline earth ions, in particular magnesium but also calcium, strontium and barium. Other examples include the ions of rare earths, in particular of gadolinium. Another group of ions are the aluminium, gallium, indium and technetium ions. The ligands used according to the invention combine particularly readily with these metals to form exceptionally stable and/or exceptionally readily soluble complex compounds. At the same time, the above mentioned metals are of great significance in the above mentioned fields of application.

The diamino derivatives of general formula V and their quaternary derivatives of general formula VI can be prepared starting from the all-cis-1,3,5-triamino-2,4,6-trihydroxycyclohexan derivatives of general formula I. In principle, a deamination reaction is carried out wherein e.g. a primary amino group is removed by forming the corresponding diazonium ion. Generally it is possible to use the methods of Ward Pigman, Carbohydrates, Academic Press, New York, 1972, Vol. I A, pages 562 ff. For example it is possible to remove a primary amino group from the correspondingly substituted 1,3,5-triamino derivative by inserting a protective group for the amino group, acylating of the hydroxyl groups, eliminating the protective group of the amino group, reaction with nitrous acid via the diazonium ion to desaminate and further removing the O-acyl groups by hydrolysis. By protecting the hydroxyl groups the yield of the desaminating reaction is improved. The quaternised products of general formula VI can be achieved by quaternising the derivatives of general formula V as described above for the derivatives of formula I.

EXAMPLE 1

Synthesis of all-cis-1,3,5-Tris-(dimethylamino)-cyclohexanetriol (A) Preparation of the starting materials
1. Phloroglucinol triacetate (Heller 1912)

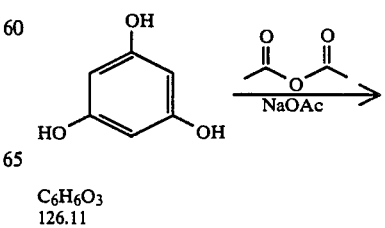

C$_6$H$_6$O$_3$
126.11

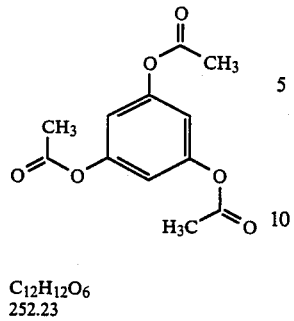

$C_{12}H_{12}O_6$
252.23

Educts:

Phloroglucinol, Fluka puriss., anhydrous, dried for 12 h in the drying cupboard at 100° C.

sodium acetate, anhydrous, dried for 12 h in the drying cupboard at 160° C.

300 g (2.85 mol) of phloroglucinol and 300 g (3.66 mol) of sodium acetate are suspended in 1.7 l (18 mol) of acetic anhydride in a 3-l round bottomed flask equipped with magnetic stirrer and Dimroth reflux condenser. The suspension is heated to 130° C. in a silicone oil bath. The suspension is stirred for 2 hours at this temperature and then left to cool. The contents, which have solidified to a white paste, are poured out on 10 kg of ice. The suspension is then vigorously stirred several times with a glass rod and finally suction filtered. The solid product is thoroughly washed twice by suspending it in 2 l of water in a 5-l glass beaker, thoroughly stirring it with a glass rod and then passing it through a suction filter.

The crude product is recrystallised twice by dissolving it in 2 l of boiling ethanol, leaving it to stand at 0° C. for at least 12 hours and then passing it through a suction filter. The purified product is left to dry at room temperature and 0.01 Torr for one day. The yield is more than 570 g (2.26 mol=95%). A further quantity of product can be obtained from the mother liquor. Phloroglucinol acetate obtained by this method melts at 106° C. (figure given in the literature: 105°–106° C.).

2. tri-Barium-bis-(trinitrophloroglucinol acetate) (Nietzki 1893, Benedikt 1878)

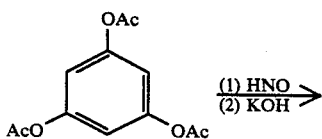

$C_{12}H_{12}O_6$
252.23

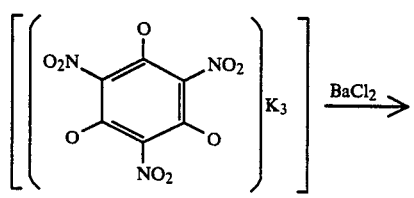

$(C_6N_3O_9)K_3$
375.38

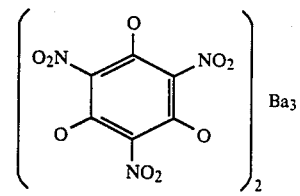

$(C_6N_3O_9)_2Ba_3$
928.18

A 1-l glass beaker is equipped with a magnetic stirrer, thermometer and cooling bath in a sand bath behind a protective screen. 400 ml (600 g, 9.5 mol) of fuming nitric acid (fuming nitric acid 100%, density about 1.52) are then cooled to 0° C. in this beaker, using a freezing mixture of ice and salt. The acid continues to be carefully cooled while 100 g (0.4 mol) of finely powdered phloroglucinol triacetate are introduced in small portions at such a rate that the temperature never rises above 15° to 20° C. Nitrous gases escape during this addition which takes about 2 hours.

The clear, brownish red solution is then poured out on 1 kg of ice in a 3-l glass beaker. A yellowish green solid (trinitrophloroglucinol triacetate) precipitates. A 50% KOH solution (1.3 kg corresponding to 650 g (11.6 mol) of KOH in 650 ml of water) is then added with cooling and stirring with a glass rod until the colour changes from golden yellow to deep red brown and a strong alkaline reaction (pH>10) can be detected. In the course of the process of neutralisation, the temperature rises to about 60° C. and the substance foams up with liberation of nitrous gases.

The cold suspension, which is at a temperature of about 20° C. and has a faint odour of ammonia, is filtered through a glass suction filter (G4). The filtrate is discarded and the solid residue, consisting of tripotassiumtrinitrophloroglucinate and potassium nitrate, is dissolved in 3 l of hot water in a 5-l round bottom flask. A solution of 250 g (1.2 mol) of barium chloride (BaCl$_2$.2-H$_2$O) in 1 l of water is added dropwise to the hot solution with vigorous stirring with a magnetic stirrer. The addition of barium chloride covers a period of 5–10 minutes and a microcrystalline, yellow solid precipitates. Stirring of the suspension is continued for a further 10 minutes and the suspension is then suction filtered. The residue is suspended in 2 l of water, stirred for 15 minutes and again suction filtered. The product is washed with ethanol and dried under a high vacuum of 0.01 Torr at room temperature. Drying to constant weight takes about 24 hours. The yield is 100 to 125 g (0.11 to 0.13 mol) of the barium salt.

3. Trinitrophloroglucinol (Nietzki 1893, Benedikt 1878)

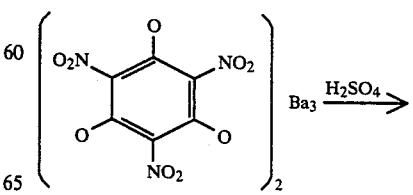

$(C_6N_3O_9)_2Ba_3$
928.18

-continued

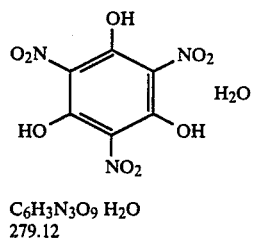

C₆H₃N₃O₉ H₂O
279.12

100 g (0.11 mol) of tri-barium-bis-(trinitrophloroglucinate) are suspended in 2.5 l of water in a 5-l round bottomed flask equipped with magnetic stirrer. 340 ml (0.34 mol) of 1M aqueous sulphuric acid are added to the suspension with stirring. The mixture continues to be stirred for at least a further 6 hours and is then filtered through Celite. A slight improvement in yield can be obtained by washing the residue. For this purpose, the barium sulphate which has been filtered off is suspended in 500 ml of water in a glass beaker together with the Celite and stirred for 15 minutes. The solid is centrifuged off and the supernatant solution is passed through a suction filter coated with Celite. The residue is again suspended in water and the process is repeated until the supernatant solution obtained after centrifuging is virtually colourless (2 to 3 times).

The combined filtrates are evaporated down to 100 ml on a rotary evaporator at a bath temperature of 30° to 40° C., and a yellow solid precipitates. The suspension is transferred to a 1-l pear-shaped flask and heated to 98° C. on a water bath. Water is added in small portions until the suspension just completely dissolves. The hot solution is then passed through a suction filter preheated with hot air, and is slowly left to cool to 4° C. Trinitrophloroglucinol hydrate crystallises in large, yellow needles which are separated from the mother liquor by suction filtration and dried in a water jet vacuum at room temperature.

Yield: 60 g (0.21 mol) of trinitrophloroglucinol.

Additional product may be obtained from the mother liquor but working up this additional product is only worth while when dealing with relatively large quantities. 10M KOH solution is added to the solution with stirring until the reaction is strongly alkaline (pH>13). Solid, golden yellow tripotassium trinitrophloroglucinate precipitates. The suspension is left to stand at 4° C. for 12 hours and then suction filtered. The solid substance is dissolved in hot water (<80° C.) and barium chloride solution is added until precipitation is complete. The tri-barium-bis-(trinitrophloroglucinate) obtained is reacted with aqueous sulphuric acid as described above. Trinitrophloroglucinol is obtained in a pure form.

(B) all-cis-1,3,5-Triammonio-2,4,6-cyclohexanetriol sulphate (Quadbeck 1956, Lichtenthaler 1966)

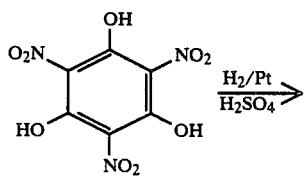

C₆H₃N₃O₉ H₂
279.12

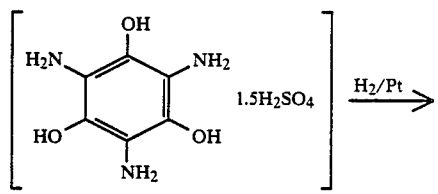

C₆H₉N₃O₃ 1.5H₂SO₄
318.27

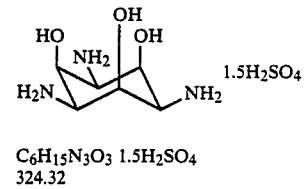

C₆H₁₅N₃O₃ 1.5H₂SO₄
324.32

About 4.4 g (18 mmol) of freshly prepared platinum dioxide hydrate are introduced into 255 ml of 1M aqueous sulphuric acid in a 2 l glass autoclave equipped with plastics stirrer. Prehydrogenation is carried out under a hydrogen pressure of 10 bar with vigorous stirring. This reduction takes a few minutes and its completion is indicated by the coagulation of black platinum.

The autoclave is then opened and 47 g (168 mmol) of solid trinitrophloroglucinol are added. The suspension is hydrogenated under a hydrogen pressure of 10 bar with cooling and vigorous stirring. The first stage (reduction of the nitro groups) proceeds relatively rapidly and with liberation of a considerable quantity of heat. Cooling is no longer required in the second stage (hydrogenation of the aromatic compounds). the end of the first stage is recognized by the disappearance of the yellow colour.

The time required for reduction depends to a large extent on the intensity of stirring. The reaction time given is that obtained with a mechanically driven stirrer operating at a speed of 1200 revs/min. A white solid substance precipitates after some time. The reaction is stopped after 10 days and the suspension is transferred to a 5 l round bottomed flask. The suspension is diluted to a volume of 3.5 l with water and stirred until the white solid has completely dissolved. Catalyst is separated by filtration through a G4 suction filter and the virtually colourless filtrate is concentrated by evaporation to 500 ml on a rotary evaporator. 1M sulphuric acid is added to the suspension until the pH has been adjusted to about 2. 1.2 l of methanol are added and the suspension is left to stand for at least 12 hours at 4° C. before it is suction filtered. The product is recrystallised 6 times as follows: It is dissolved in the minimum quantity (about 1.6 l) of water (25° C.) and filtered through a G4 suction filter, and 750 ml of methanol are slowly added to the solution with stirring. The suspension is left to stand overnight at 4° C. and the solid is separated from the mother liquor by suction filtration. The product is dried, first in a drying cupboard at 80° C. and then to constant weight under a vacuum of 0.01 Torr at 80° C.

The yield is 27 g (84 mmol) which corresponds to 50% of the trinitrophloroglucinol put into the process.

The hydrated platinum dioxide required may, for example, be prepared before each reaction from ammonium hexachloroplatinate(IV) by a modified method of organic syntheses (Adams (1964)) as follows:

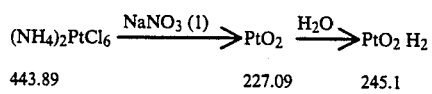

A mixture of 100 g of sodium nitrate and 8 g of ammonium hexachloroplatinate is weighed into a 250 ml beaker of Pyrex glass (the use of potassium nitrate described in Organic Syntheses (1964) causes the glass beaker to crack during the reaction). The mixture is heated in an open crucible in a sand bath. The temperature may be controlled with a calibrated Chromel-Alumel-Thermoelectric element (Handbook 1974). The mixture turns brown and melts with vigorous evolution of gas. Foaming and spraying can be prevented by stirring with a glass rod. A highly mobile melt is finally obtained, which is heated to 500°–540° C. (19.8–21.5 mV, Ref.=20° C.) for 30 minutes. The liquid solidifies when subsequently cooled. At least 150 ml of water are added to the cold contents which are then stirred until all the sodium nitrate has dissolved. The dark brown solid substance is separated from the nitrate solution by filtration through a G4 suction filter and used without drying or characterisation.

Rinsing with nitrogen must be carried several times before and after contact of the platinum catalyst with hydrogen.

The reaction mixture must not come into contact with parts of apparatus made of (stainless) steel because the iron dissolved by corrosion during the reaction would then undergo complex formation together with the end product obtained. Such metal complexes would be difficult to separate afterwards.

EXAMPLE 2 all-cis-1,3,5-Tris-(dimethylammonio)-cyclohexanetriol-trichloride dihydrate

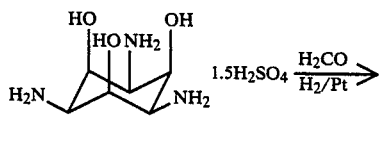

$C_6H_{15}N_3O_3 \cdot 1.5H_2SO_4$
324.32

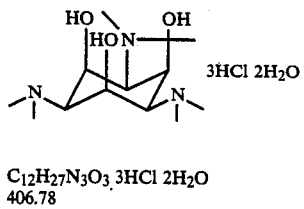

$C_{12}H_{27}N_3O_3 \cdot 3HCl \cdot 2H_2O$
406.78

About 2.2 g (9.0 mMol) of freshly prepared platinum dioxide hydrate are suspended in 200 ml of water. The suspension is prehydrogenated for 15 minutes in a 2-l glass autoclave at room temperature under a 10 bar pressure with vigorous stirring (1200 revs/min).

The autoclave is then opened and 15 g (46.3 mMol) of all-cis-triaminio-cyclohexanetriol sulphate and 40 g (533 mMol) of 40% aqueous formaldehyde solution are added. Hydrogenation is then continued for 24 hours at 10 bar at room temperature. The autoclave is then again opened and the pH of the solution tested. If the reaction is found to be distinctly acid (pH>4), hydrogenation must be continued for a further 24 hour. If it is not distinctly acid, the reaction mixture is transferred to a 2 l glass beaker and the catalyst is separated off by means of a G4 suction filter. The filtrate is evaporated to dryness on a rotary evaporator, dissolved in 100 ml of water and applied to an ion exchange column Dowex 1, Cl− form (dimensions of column: Length 30 cm, diameter 3 cm, ion exchange resin: Dowex 1, ×4. 50/100 mesh, chloride form: activation and regeneration: elute with 2 l of 2M HCl and then with water until the eluate is neutral in reaction). Elution is continued until the filtrate is free from chloride and the filtrate is tested with dilute barium chloride solution on sulphate. If any precipitation of barium sulphate is observed, the ion exchange must be repeated on a regenerated column. The solution is then evaporated to dryness on a rotary evaporator and the colourless residue is recrystallised from the minimum quantity of boiling methanol (about 300 ml). An additional quantity of product is obtained from the mother liquor by evaporating this to dryness and recrystallising the residue from boiling methanol. Both fractions are washed with ether and dried for 12 hours at 0.01 Torr and room temperature. Yield: 12 g (29.5 mMol)=63.7%.

EXAMPLE 3 all-cis-1,3,5-Tris-(dimethylamino)-2,4,6-cyclohexanetriol

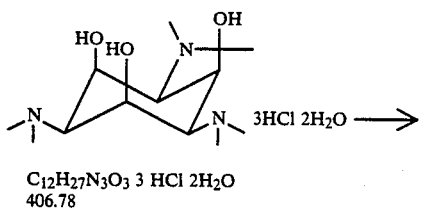

$C_{12}H_{27}N_3O_3 \cdot 3HCl \cdot 2H_2O$
406.78

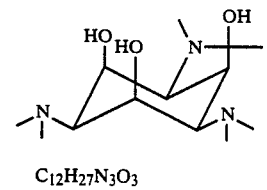

$C_{12}H_{27}N_3O_3$
261.37

12 g (29.5 mMol) of tris-(dimethylammonio)-cyclohexane triol-tri-chloride dihydrate dissolved in 100 ml of water are applied to an ion exchange column Dowex 1, OH form (column dimensions: Length 30 cm, diameter 3 cm; ion exchange resin: Dowex 1, ×4, 50/100 mesh; activation and regeneration: elute with 2 l of 2M hydrochloric acid, wash with water until the eluate is neutral in reaction; elute with 2 l of 0.2M NaOH solution (use water free from $CO_2$) (eluate must finally react alkaline); elute with water free from $CO_2$ until the eluate is neutral in reaction). Elution with water is continued until the eluate is neutral in reaction. After concentration by evaporation on a rotary evaporator, a white solid is obtained (all-cis-1,3,5-tris-(dimethylamino)-cyclohexane-triol-hydrate $C_{12}H_{27}N_3O_3\cdot H_2O$). This solid is boiled in 500 ml of hexane under reflux for 30 minutes. 200 ml of solvent are then distilled off (azeotropic mixture of water-hexane) and the hot solution is filtered through a paper filter. A further 150 ml are then distilled off.

The filtrate is left to stand for 24 hours at 4° C. A colourless solid crystallises, and this solid is again recrystallised from 150 ml of boiling hexane. The product is suction filtered and dried to constant weight at 0.01 Torr and room temperature.

7 g (26.8 mMol) of anhydrous tris-(dimethylamino)-cyclohexane triol are obtained.

Physical parameters of the products obtained in the above examples

Phloroglucinol triacetate (9)
Mp: 106° C.

| Analysis: $C_{12}H_{12}O_6$ | | |
|---|---|---|
| | C | H |
| Calculated | 57.14% | 4.80% |
| Found | 57.07% | 4.79% |

$^1$H-NMR (90 MHz, CDCl$_3$): 6.84 ppm (s, 3H), 2.23 ppm (s, 9H).
$^{13}$C-NMR (62.9 MHz, CDCl$_3$, broad band decoupled): 168.4 ppm, 151.1 ppm, 112.7 ppm, 20.8 ppm.
Trinitrophloroglucinol (4)
Mp: 167° C. (decomposition, see Defusco (1982)).
all-cis-1,3,5-Triammonio-2,4,6-cycLohexanetriol sulphate(10a)

| Analysis: $C_6H_{15}N_3O_3$ 1.5 $H_2SO_4$ | | | | |
|---|---|---|---|---|
| | C | H | N | S |
| Calculated | 22.22 | 5.59 | 12.96 | 14.83 |
| Found | 22.22 | 5.69 | 12.80 | 14.91 |

$^1$H-NMR (90 MHz, D$_2$O): 4.8 ppm (s, HDO), 4.5 ppm (m, 3H), 3.8 ppm (m, 3H).
$^{13}$C-NMR (62.9 MHz, D$_2$O, broad band decoupled): 65.6 ppm, 50.5 ppm.

EXAMPLE 4 all-cis-1,3,5-Triammonio-2,4,6-cyclohexanetriol trichloride (10b)

An aqueous, saturated solution of the sulphate (10a) was chromatographed on an anion exchange resin (Dowex 1, Cl form). The solution was evaporated to dryness on a rotary evaporator and dissolved in the minimum quantity of water. The desired chloride (10b) crystallised on introduction of hydrogen chloride. The yield was virtually quantitative.

$^1$H-NMR (90 MHZ, D$_2$O): identical with (10a)

EXAMPLE 5 all-cis-1,3,5-Triamino-2,4,6-cyclohexanetriol (1)

(a) An aqueous, saturated solution of 303 mg (0.93 mMol) of sulphate (10a) was introduced into an anion exchange column (Dowex 1, OH form). The solution was eluted with water until the eluate was neutral in reaction. Concentration by evaporation on a rotary evaporator yielded a colourless solid which was recrystallised from 50 ml of boiling ethanol. 70 mg (0.36 mMol), 38%) of amine were obtained.

(b) 5.93 g (18.3 mMol) of sulphate (10a) were dissolved in 1 l of water. 281 ml of 9.76·10$^{-2}$M barium hydroxide solution were added and the mixture was left to stand for 12 hours and then filtered through Celite.

The colourless solution was evaporated to dryness on a rotary evaporator. A colourless solid was obtained.

The two products could not be distinguished by conventional methods of characterisation.

Mp: Discolouration from about 150° C., charring at 200°-210° C. (Lichtenthaler (1966): 203°-204° C.)
$^1$H-NMR (90 mHz, D$_2$O):
4.8 ppm (s, HDO), 3.83 ppm (m, 3H), 2.80 ppm (m, 3H).
$^{13}$C-NMR (62.9 MHz, D$_2$O, broad band decoupled): 73.7 ppm, 51.7 ppm.

EXAMPLE 6 all-cis-1,3,5-Triammonio-2,4,6-cyclohexanetriol triformate (10c)

6.75 g (20.8 mMol) of sulphate (10a) were dissolved in 1 l of water and chromatographed on an anion exchange resin (Dowex 1, formate form).

The eluate was evaporated to an oil on a rotary evaporator (tendency to bumping and delayed boiling), and taken up in a small quantity of water. Acetone was then added until cloudiness appeared. A colourless crystallisate was obtained at 4° C.

Yield: 4.63 g (14.7 mMol, 71%).

| Analysis: $C_9H_{21}N_3O_9$ | | | |
|---|---|---|---|
| | C | H | N |
| Calculated | 34.29% | 6.71% | 13.33% |
| Found | 34.00% | 6.84% | 13.00% |

Physical parameters of the products prepared in the above examples:

all-cis-1,3,5-Tris-(dimethylammonio)-2,4,6-cyclohexanetriol trichloride dihydrate (12a)

| Analysis: $C_{12}H_{27}N_3O_3\cdot 3HCl\cdot 2H_2O$ | | | | |
|---|---|---|---|---|
| | C | H | N | Cl |
| Calculated | 35.43% | 8.42% | 10.33% | 26.15% |
| Found | 35.28% | 8.04% | 10.23% | 26.40% |

$^1$H NMR (90 MHz, D$_2$O): 5.0 ppm (m, 3H), 4.8 ppm (s, HDO), 3.6 ppm (m, 3H), 3.2 ppm (s, 18H).
$^{13}$C-NMR (62.9 MHz, D$_2$O, broad band decoupled): 64.6 ppm, 61.8 ppm, 42.4 ppm.
all-cis-1,3,5-Tris-(dimethylamino)-2,4,6-cyclohexantriol (11)
Mp: 118°-119° C.

| Analysis: $C_{12}H_{22}N_3O_3$ | | | |
|---|---|---|---|
| | C | H | N |
| Calculated | 55.15% | 10.41% | 16.08% |
| Found | 55.08% | 10.34% | 15.96% |

$^1$H-NMR (90 MHz, CDCl$_3$): 4.35 ppm (m, 3H), 3.8 ppm (m, 3H), 2.47 ppm (s, 18H), 1.73 ppm (m, 3H).

Shaking with D$_2$O resulted in the following changed signals: 4.7 ppm (s) new, 4.35 ppm (m, 3H), no signal in the 3.5–4.0 ppm range.

$^1$H-NMR (90 MHz, D$_2$O): 4.80 ppm (s, HDO), 4.63 ppm (m, 3H), 2.45 ppm (s, 18H), 2.05 ppm (m, 3H).
$^{13}$C-NMR (62.9 MHz, D$_2$O, broad band decoupled): 66.6 ppm, 66.3 ppm, 42.3 ppm.

EXAMPLE 7 all-cis-1,3,5-Tris-(dimethylammonio)-2,4,6-cyclohexanetriol sulphate (12b)

The sulphate (12b) was obtained by stoichiometric reaction of the amine (11) with dilute sulphuric acid. In contrast to the chloride (12a) it is virtually insoluble in boiling methanol.

$^1$H-NMR (90 MHz, D$_2$O): identical to (12a).

EXAMPLE 8

Methylation of of all-cis-1,3,5-triammonio-2,4,6-cyclohexane-triol triformate with formaldehyde and formic acid all-cis-1,3,5-Tris-(dimethylammonio)-2,4,6-cyclohexane-triol-trichloride dihydrate (12a)

13 g (38 mMol) of formate (10c), 25 g (about 0.5 mol) of formic acid (98 to 100%) and 25 g (0.33 mol) of aqueous, 40% formaldehyde solution were dissolved in 70 ml of water. The solution was heated at 120° C. under reflux for 18 hours. A further 10 g (0.13 mol) of formaldehyde solution were added 5 hours after the start. The clear solution was then concentrated by evaporation on a rotary evaporator and the residue was taken up with 200 ml of ethanol. Anhydrous hydrogen chloride was then introduced over a period of one hour, and a white solid crystallised. The reaction mixture was left to stand overnight at 4° C. and suction filtered. The crystallisate was washed with alcohol and ether and dried in a high vacuum.

Yield: 4.5 g (11 mMol, 29%) (12a).

The instrumental analytical characteristics of this product were indentical to those of the preparation described in Example 6.

EXAMPLE 9

Quaternisation of 1,3,5-tris-(dimethylamino)-2,4,6-cyclohexanetriol (11)

Quaternisation with methyl iodide

Quaternisation was carried out in methanol, acetonitrile and nitromethane at room temperature or at reflux. The triquaternary compound was obtained in a pure form by recrystallisation.

$^1$H-NMR spectrum of the monoquaternary compound (17): (90 MHz, D$_2$O), 5.0 ppm (m, 2H), 4.8 ppm (s, HDO), 4.7 ppm (m, H), 3.5 ppm (s, 9H), 3.4 ppm (t, 1H), 2.5 ppm (s, 12H), 2.2 ppm (m, 2H).

$^1$H-NMR spectrum of the diquaternary compounds (18) (90 MHz, D$_2$O), 5.45 ppm (m, 1H), 5.1 ppm (m, 2H), 4.8 ppm (s, HDO), 3.55 ppm (s, 18H), 3.45 (m, 2H), 2.6 ppm (s, 6H), 2.35 ppm (m, 1H).

EXAMPLE 10 all-cis-1,3,5-Tris-(trimethyylammonio)-2,4,6-cyclohexanetriol triiodide (19a)

(a) 200 mg (0.77 mMol) of anhydrous triamine (11) were dissolved in 2 ml of nitromethane, and 500 mg (3.5 mMol) of methyl iodide were then added. A white solid crystallised. The reaction mixture continued to be stirred for 24 hours at room temperature and was then evaporated to dryness on a rotary evaporator. After drying in a high vacuum, the product was found to be pure (19a).

(b) 10 g (18 mMol) of diquaternary (18) were suspended in 80 ml of methanol and 20 ml of water. 10 g (70 mMol) of methyl iodide were added and the reaction mixture was boiled under reflux for 24 hours. It was then evaporated to dryness on a rotary evaporator and recrystallised three times as follows: The solid was suspended in 40 ml of water. 0.1M NaOH solution was then added until the pH was about 8 to 9. The reaction mixture was heated until it was completely dissolved, and 100 ml of methanol were added. Colourless crystals were obtained at 0° C. The compound may also be recrystallised from boiling water.

| Analysis: C$_{15}$H$_{36}$I$_3$N$_3$O$_3$.0.5H$_2$O | | | |
|---|---|---|---|
| | C | H | N |
| Calculated | 25.88% | 5.36% | 6.04% |
| Found | 25.63% | 5.10% | 6.03% |

$^1$H-NMR (90 MHz, D$_2$O): 5.6 ppm (m, 3H), 4.8 ppm (s, HDO), 3.7 ppm (m, 3H), 3.6 ppm (s, 27H)

EXAMPLE 11 all-cis-1,3,5-Tris-(ammoniomethanephosphonic acid)-2,4,6-cyclohexanetriol trichloride

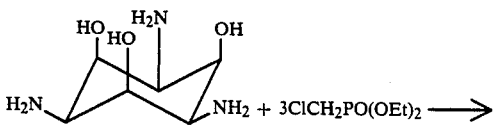

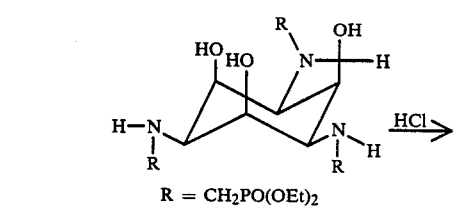

R = CH$_2$PO(OEt)$_2$

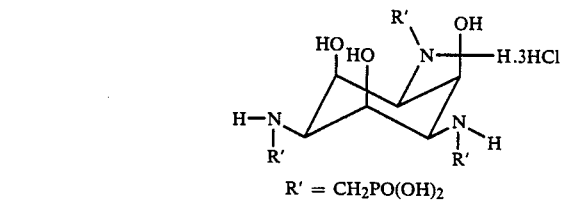

R' = CH$_2$PO(OH)$_2$ 0.468 ml (3 mMol) of the diethylester of chloromethane phosphonic acid was added to a solution of 177 mg (1 mMol) of all-cis-1,3,5-triamino-2,4,6-cyclohexanetriol in 25 ml of water and the reaction mixture was boiled at reflux in the dark for 6 days under nitrogen. All-cis-1,3,5-tris(ammoniomethanephosphonic acid diethylester)-2,4,6-cyclohexanetriol trichloride was obtained in a yield of about 80%.

$^1$H-NMR (250 MHz, D$_2$O, pD 4): 1.17 ppm (t), 3.19 ppm (m), 3.41 ppm (d), 3.88 ppm (m), 4.45 ppm (m)

$^{31}$P-NMR (100 MHz, D$_2$O, pD 4): 15.5 ppm $^{13}$C-NMR (02.9 MHz, D$_2$O, pD 4): 15.9 ppm, 34.6 ppm, 50.4 ppm, 62.0 ppm, 65.2 ppm.

all-cis-Tris-(ammoniomethanephosphonic acid)-2,4,6-cyclohexanetriol trichloride is obtained by several hours' boiling under reflux in conc. HCl.

pK-values (approximate): 5.2, 6.0, 6.5, 7.0, 8.0, 9.5

Response to iron:

At pH 7.5, the ligand keeps iron(III) in solution (maximum 2 Fe(III) per ligand). A solution containing Fe(III):ligand=0.9:1 is clear in the pH range of 2 to 12. The complex is relatively difficult to dissolve at pH 3-4.

EXAMPLE 12 all-cis-1,3,5-Tris-(2'-ammoniopropionic acid)-2,4,6-cyclohexanetriol trichloride

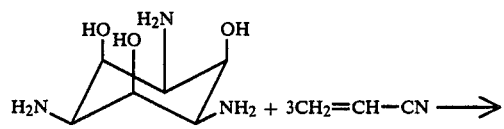 + 3CH$_2$=CH—CN ⟶

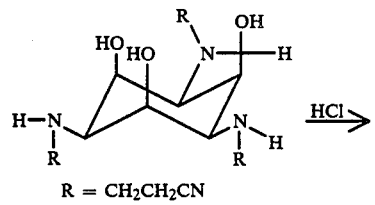

R = CH$_2$CH$_2$CN $\xrightarrow{HCl}$

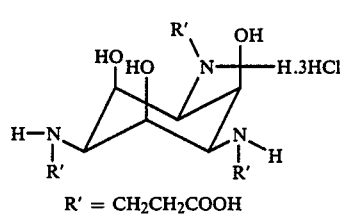

R' = CH$_2$CH$_2$COOH 3 ml of a 1M acrylonitrile solution (3 mMol) were added to a solution of 0.177 g (1 mMol) of all-cis-1,3,5-triamino-2,4,6-cyclohexanetriol in 40 ml of water which was then left to stand in the dark under N$_2$ for one week. Concentration by evaporation on a rotary evaporator yielded the intermediate product, all-cis-1,3,5-tris-(2'-aminopropionitrile)-2,4,6-cyclohexanetriol.

$^1$H-NMR (90 MHz, D$_2$O, pD 2): 4.54 ppm (m, 3H), 3.60 ppm (m, 3H), 3.49 ppm (t, 6H), 2.98 ppm (t, 6H).

$^{13}$C-NMR (62.9 MHz, D$_2$O, pD 3): 14.9 ppm, 40.6 ppm, 57.0 ppm, 63.2 ppm, 117.4 ppm.

pK-values (approximate): 3.0, 4.5, 6.3.

The nitrile was hydrolysed by boiling under reflux in conc. HCl for 3 hours. Concentration by evaporation on a rotary evaporator yielded all-cis-1,3,5-tris-(2'-ammoniopropionic acid)-2,4,6-cyclohexanetriol trichloride.

$^{13}$C-NMR (62.9 MHz, D$_2$O, pD 4): 32.1 ppm, 42.3 ppm, 56.4 ppm, 63.1 ppm, 178.2 ppm.

pK-values (approximate): 6.2, 8.2, 9.7.

Response to iron(III):

At pH 7.5, a ligand molecule holds at the most 2 Fe(III) in solution. A solution containing Fe(III):ligand=1:1 is clear over the entire ranges of pH. In the range of pH 3 to 6, the complex is relatively sparingly soluble.

EXAMPLE 13 all-cis-1,3,5-Tris-(ammonioacetic acid)-2,4,6-cyclohexanetriol trichloride

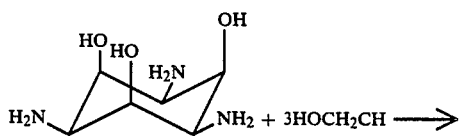 + 3HOCH$_2$CH ⟶

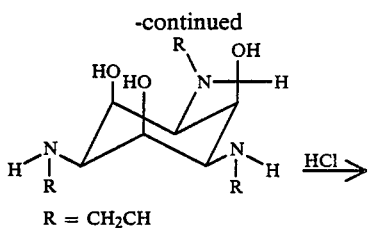

R = CH$_2$CH $\xrightarrow{HCl}$

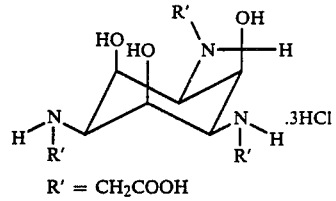 .3HCl

R' = CH$_2$COOH 0.0975 g of all-cis-1,3,5-triammonio-2,4,6-cyclohexanetriol sulphate (0.3 mMol) were dissolved in 60 ml of water and neutralised with 4.5 ml of KOH 0.2M (0.9 mMol). 0.0514 g of freshly distilled glycollic acid nitrile (0.903 mMol) was added and the clear solution was left to stand in the dark under nitrogen for 6 days. The faintly yellow solution was evaporated to dryness on a rotary evaporator.

$^{13}$C-NMR (62.9 MHz, D$_2$O): 33.8 ppm 57.7 ppm, 68.9 ppm, 119 ppm (broad)

pK-values (approximate): 6.5, the next lowest about 3.

The product was boiled overnight under reflux in 20 ml of conc. HCl. After concentration of the product by evaporation it was dried to constant weight.

pK-values (approximate): three lower than 3, 5.7, 7.8, 8.9.

Response to iron(III):

Solutions having a ligand:iron ratio of 1:1 remain clear at pH values from 2 to about 11. Iron hydroxide precipitates at higher pH values.

EXAMPLE 14 all-cis-1,3,5-(N-methylammonioacetic acid)-2,4,6-cyclohexanetriol trichloride 0.5 mMol of all-cis-1,3,5-tris-(aminoacetic acid nitrile)-2,4,6-cyclohexanetriol (intermediate product from Example 13) were dissolved in 20 ml of methanol. 282 mg of Methyl iodide (2 mMOl), 2 mMol of KHCO$_3$ and 2 mMol of K$_2$CO$_3$ were added. The mixture was boiled under reflux overnight. After evaporation to dryness and acidification to pH 1 with HNO$_3$, titration with AgNO$_3$ showed an iodide content of 80% of the theoretical value for all-cis-1,3,5-tri-(N-methylammonioacetonitrile)-2,4,6-cyclohexanetriol triiodide. This shows that methylation was not complete. The nitrile was subsequently hydrolysed to the acid by boiling under reflux in 20 ml of conc. HCl.

Response to β-FeO(OH): The compound dissolves this rust in a ratio of 1:1.

EXAMPLE 15 all-cis-1,3,5-(N-butylammonioacetic acid)-2,4,6-cyclohexanetriol trichloride

Preparation as in Example 14 but using 0.27 g of n-butyl bromide instead of methyl iodide. Titration with AgNO$_3$ gave a value close to the theoretical value.

Response to β-FeO(OH): Identical to Examples 13 and 14.

EXAMPLE 16

Synthesis of all-cis-1,3,5a-tris-(succinoylamino)-2,4,6-cyclohexanetriol

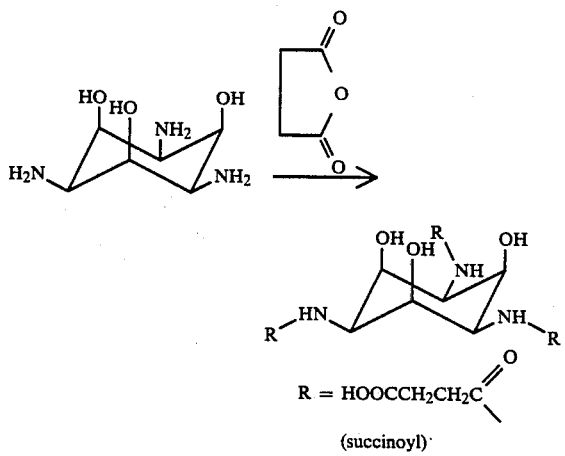

R = HOOCCH₂CH₂C(=O)—
(succinoyl)

10 g (0.057 mol) of all-cis-triamino-cyclohexanetriol are dissolved in 100 ml of water. 18.7 g (0.187 mol) of succinic acid anhydride are dissolved in the minimum quantity of water and slowly added. The reaction mixture is stirred for 30 minutes and then concentrated by evaporation to about 20 ml. The pH is about 6.0. 300 ml of DMSO are added and the remaining quantity of water is evaporated off under vacuum. The DMSO is left in the precipitate when all the water has been removed. This precipitate is filtered off and dried (about 16 hours in a high vacuum) until the substance is free from DMSO.

Yield

1st Fraction: 7.3 g (0.015 mol) of product ≙ 28%. A further quantity of product may be obtained from the mother liquor by evaporation and filtration.

Melting point: >300° C.

Solubility: Readily in water, water/MeOH, water/EtOH, sparingly in cyclohexane

UV: max 212 nm

IR: CONH: 1650, 1555

EXAMPLE 17

Synthesis of all-cis-1,3,5-tris-(octanoylamino)-cyclohexanetriol

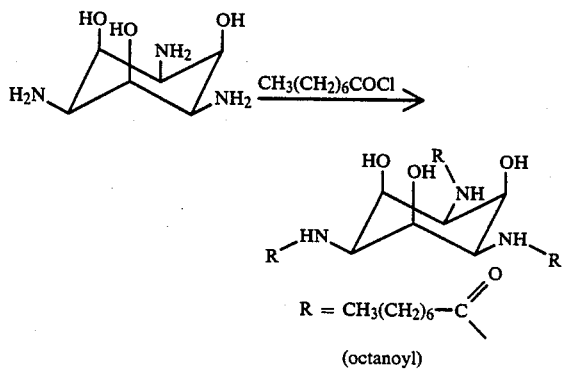

R = CH₃(CH₂)₆—C(=O)—
(octanoyl)

6 g (0.018 mol) of all-cis-triamino-cyclohexanetriol are dissolved in the minimum quantity of water in a glass beaker. 20 ml (0.123 mol) of caprylic acid chloride are added and the mixture is stirred. An excess of 1:2.3 is required for obtaining a good yield. 10N-sodium hydroxide solution is then added with vigorous stirring until a white precipitate is formed (partly NaCl, partly product). The sodium chloride is dissolved by the addition of water but the product remains as precipitate. The product is insoluble in water. The precipitate is filtered off and again washed with water. For further purification, the product is dissolved in MeOH and again precipitated from water.

Yield: 6.0 g of product, corresponding to 0.011 mol ≙ 60%

Melting point: >300° C.

Solubility: readily in EtOH, CHCl₃, Tween and MeOH, insoluble in H₂O

UV: maximum at 212 nm

IR: CONH: 1630 and 1530.

Pharmacological action all-cis-1,3,5-Triamino-2,4,6-cyclohexanetriol (10), all-cis-1,3,5-tris-(dimethylamino)-2,4,6-cyclohexane triol hydrochloride (12a), all-cis-1,3,5-tris-(trimethylammonio)-2,4,6-cyclohexanethiol (19c) and all-cis-1,3,5-tris-(succinoylamino)-2,4,6-cyclohexanetriol are found to have the following values in mg/kg of body weight in the orientating LD₅₀-toxicity test on white mice after intravenous injection: 158, 440, 235 and >1000. The elimination of iron from rats with an excessively high iron level by excretion in the urine and faeces after intravenous administration is shown in the following Table by comparison with the figures obtained with Desferal. The rates of excretion were measured over 72 hours after application.

| Substance | Urine | Faeces |
|---|---|---|
| Desferal | 1 | 1 |
| 10 | 0.1 | 0.2 |
| 12a | 1 | 0.5 |
| 19c | 0.2 | 0.5 |

We claim:

1. An all-cis-1,3,5-triamino-2,4,6-trihydroxycyclohexane compound corresponding to the formula I:

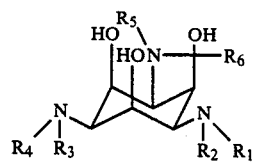

wherein $R_1$, $R_2$, $R_3$, $R_4$, $R_5$ and $R_6$ are the same or different and each represent hydrogen, alkyl groups or —CO-alkyl groups wherein the alkyl in the alkyl or —CO-alkyl group contains 1 to 18 carbon atoms and the alkyl and —CO-alkyl groups may independently contain at least one functional group capable of coordinating with metal cations, and at least one of the group $R_1$ to $R_6$ is a substituted or unsubstituted alkyl or —CO-alkyl group, or a salt thereof with a pharmaceutically acceptable inorganic or organic acid, or a quaternary ammonium salt thereof corresponding to the formula II, IIa or IIb:

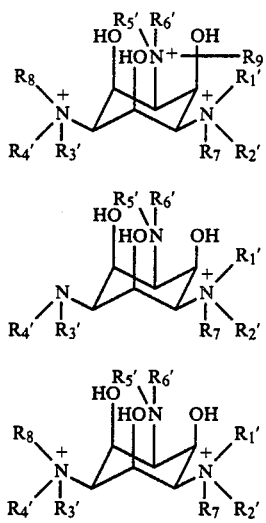

with a pharmaceutically acceptable anion, wherein $R_1'$ to $R_6'$ and $R_7$, $R_8$ and $R_9$ independently denote substituted or unsubstituted alkyl groups or —CO-alkyl groups as defined above, with the proviso that when $R_2$, $R_4$ and $R_6$ are all hydrogen, at least one of $R_1$, $R_3$ and $R_5$ must be other than —CO—CH$_3$.

2. A compound according to claim 1, wherein the alkyl in said alkyl or —CO-alkyl groups contains from 1 to 12 carbon atoms.

3. A compound according to claim 2, wherein the alkyl in said alkyl or —CO-alkyl groups contains from 1 to 6 carbon atoms.

4. A compound according to claim 3, wherein the alkyl in aid alkyl or —CO-alkyl groups contains from 1 to 4 carbon atoms.

5. A compound according to claim 4, wherein the alkyl in said alkyl or —CO-alkyl groups is independently selected from the group consisting of methyl, ethyl, n-propyl, isopropyl, n-butyl and t-butyl.

6. A compound according to claim 1, wherein not more than one substituent on each nitrogen atom is a secondary alkyl group, a tertiary alkyl group or a —CO-alkyl group.

7. A compound according to claim 1, wherein at least one nitrogen atom carries a secondary alkyl substituent, a tertiary alkyl substituent or a —CO-alkyl substituent.

8. A compound according to claim 7, wherein the remaining substituents on each nitrogen atom are selected from the group consisting of hydrogen or methyl.

9. A compound according to claim 1, wherein all the groups $R_1$ to $R_6$ or $R_1$ to $R_9$ are identical alkyl groups bonded to a nitrogen through a primary carbon atom.

10. A compound according to claim 1, wherein all the groups $R_1$ to $R_6$ or $R_1$ to $R_9$ are methyl or —CO—CH$_3$ groups.

11. A compound according to claim 1, wherein the alkyl groups or —CO-alkyl groups contain at least one functional group capable of coordinating with iron(III).

12. A compound according to claim 1, wherein the alkyl groups or —CO-alkyl groups contain at least one functional group independently selected from the group consisting of —OH, —COOH and salts thereof, —CONH$_2$, —CON(OH)R wherein R is C1 to C6 alkyl, —OPO$_3$H$_2$ salts thereof, —PO$_3$H$_2$ and salts thereof, —SR wherein R is C1 to C6 alkyl, esters of the aforementioned acids, —CN,

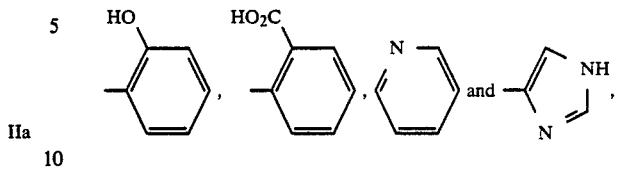

and salts thereof.

13. A compound according to claim 1, wherein $R_1$ to $R_6$ or $R_1$ to $R_9$ independently represent (a) —H,
(b) C1 to C12 alkyl or —CO-alkyl with 1 to 12 C atoms in the alkyl group,
(c) —(CH$_2$)$_n$OH,
(d) —(CH$_2$)$_n$CO$_2^-$,
(e) —(CH$_2$)$_n$CONH$_2$,
(f) —(CH$_2$)$_n$CON(OH)R wherein R is C1-C12 alkyl,
(g) —(CH$_2$)$_n$OPO$_3^{2-}$,
(h) —(CH$_2$)$_n$PO$_3^{2-}$,
(i) —(CH$_2$)$_n$SR wherein R is C1-C12 alkyl,

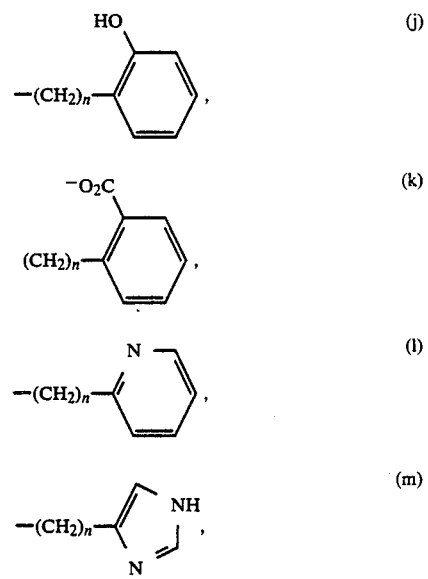

wherein n is 1, 2 or 3, and salts thereof.

14. A compound according to claim 1, wherein $R_1$ to $R_6$ or $R_1$ to $R_9$ independently represent (a) —CO—(CH$_2$)$_n$OH,
(b) —CO—(CH$_2$)$_n$CO$_2^-$,
(c) —CO—(CH$_2$)$_n$CONH$_2$,
(d) —CO—(CH$_2$)$_n$CON(OH)R wherein R is C1-C12 alkyl,
(e) —CO—(CH$_2$)$_n$OPO$_3^{2-}$,
(f) —CO—(CH$_2$)$_n$PO$_3^{2-}$,
(g) —CO—(CH$_2$)$_n$SR wherein R is C1-C12 alkyl,

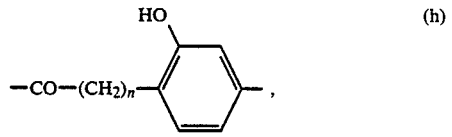

-continued

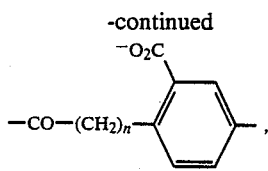  (i)

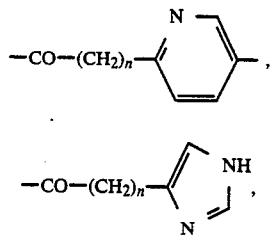  (j)

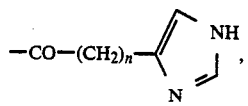  (k)

wherein n is 1, 2 or 3, or salts thereof.

15. An all-cis-1,3,diamino-2,4,6-cyclohexanetriol compound corresponding to the formula

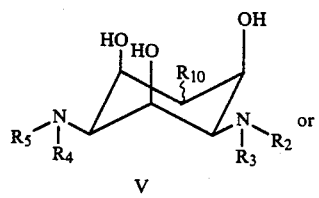  V

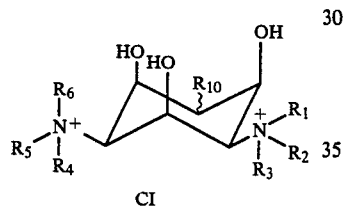  CI wherein $R_1$ to $R_6$ have the meanings set forth in claim 1 and $R_{10}$ represents —H or —OH.

16. A pharmaceutical composition comprising a conventional auxillary agent or carrier and at least one compound selected from the group consisting of all-cis-1,3,5-triamino-2,4,6-cyclohexanetriol, pharmaceutically acceptable salts thereof and compounds according to claim 1.

17. All-cis-1,3,5-Triamino-2,4,6-cyclohexanetriol compounds corresponding to the formula

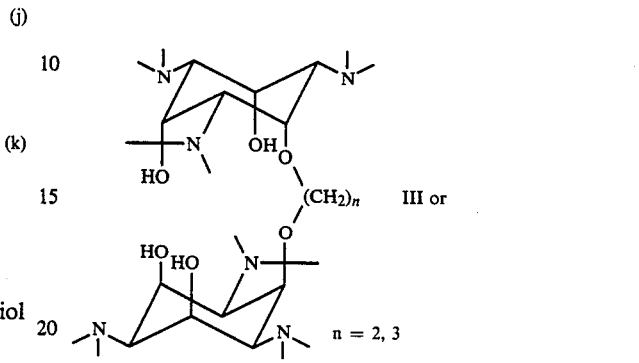  III or

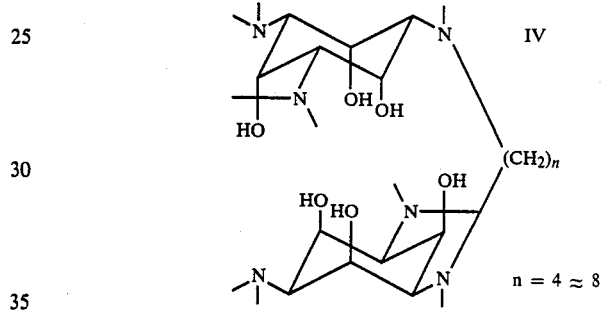  IV wherein the substituents on the nitrogen atom are H or $CH_3$, independently of one another.

18. A compound according to claim 17, wherein all the substituents on the nitrogen atom are $CH_3$ groups.

* * * * *